United States Patent [19]

Kuhla et al.

[11] Patent Number: 4,727,169
[45] Date of Patent: Feb. 23, 1988

[54] 3- AND 5-(BICYCLIC ETHER OR BICYCLIC ALKYLENE THIOETHER) ALKYLENE AMINO THIATRIAZINES, AND THEIR PHARMACEUTICAL USES

[75] Inventors: Donald E. Kuhla, Doylestown; Henry F. Campbell, Lansdale; William L. Studt, Harleysville; Stuart A. Dodson, Lansdale; Robert A. Galemmo, Jr.; Pamela J. Durham, both of Ambler, all of Pa.

[73] Assignee: Rorer Pharmaceutical Corporation, Fort Washington, Pa.

[21] Appl. No.: 10,900

[22] Filed: Feb. 4, 1987

Related U.S. Application Data

[60] Division of Ser. No. 817,852, Dec. 2, 1985, which is a continuation-in-part of Ser. No. 664,062, Oct. 23, 1984, Pat. No. 4,595,683, which is a continuation-in-part of Ser. No. 604,988, Apr. 27, 1984, abandoned.

[51] Int. Cl.$^4$ .................................................. C07F 7/10
[52] U.S. Cl. ...................................................... 556/420
[58] Field of Search ......................................... 556/420

[56] References Cited

U.S. PATENT DOCUMENTS 4,339,581  7/1982  Totten et al. ............... 556/420 X
4,631,346 12/1986  Webb et al. .................... 556/420

Primary Examiner—Paul F. Shaver
Attorney, Agent, or Firm—James A. Nicholson; Alexis Barron; Martin F. Savitzky

[57] ABSTRACT

A class of 3- and 5-amino thiatriazine compounds exhibiting pharmacological activity, including gastrointestinal anti-ulcerogenic and cytoprotective activity, pharmaceutical compositions comprising these compounds, and methods for the treatment of gastrointestinal hyperacidity and ulcerogenic disorders in mammals using said compositions.

1 Claim, No Drawings

3- AND 5-(BICYCLIC ETHER OR BICYCLIC ALKYLENE THIOETHER) ALKYLENE AMINO THIATRIAZINES, AND THEIR PHARMACEUTICAL USES

This is a divisional of co-pending application Ser. No. 817,852 filed on Dec. 2, 1985, which is a continuation-in-part of application Ser. No. 664,062, filed Oct. 23, 1984, now U.S. Pat. No. 4,595,683, issued June 17, 1986, which was a continuation-in-part of application Ser. No. 604,988, filed Apr. 27, 1984, now abandoned.

FIELD OF THE INVENTION

This invention relates to a class of thiatriazine compounds characterized by an amino substitutent in the 3- and/or the 5-position of the thiatriazine ring and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid, are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block of the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_2$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor has the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications GB No. 2067987A and GB No. 2047238A, and EPO publication No. 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl- carbamoylcarboxylic acids, esters and imides described in U.S. Pat. No. 4,321,372.

Thiatriazines are disclosed for use as herbicides, fungicides, and/or bacteriocides in U.S. Pat. Nos. 3,817,993; 4,007,175; 3,915,688; 4,013,447; 4,316,015; 4,343,648; 4,425,152 and 4,426,219; EPO Appl. Ser. Nos. EP 0073443A1 and EP 0071051A1; Ger. Pat. Nos. DE 3,013,268; DE 3,143,381; DE 3,134,145; Ger. Offen. No. 2,337,867; Ger. Offen. No. 2,933,889; E. Ger. No. 142,338; and E. Ger. No. 113,006.

Compounds of the present invention comprise amino thiatriazines which exhibit pharmaceutical activity in humans such as gastrointestinal activity including anti-ulcer activity and cytoprotective activity.

SUMMARY OF THE INVENTION

The present invention relates to a method for the therapeutic treatment of a human or other mammal comprising administering thereto a therapeutically effective amount of a 1,2,4,6-thiatriazine-1,1-dioxide compound substituted in the 3- and/or the 5-position by a N-(bicyclic ether or bicyclic alkylene thioether) alkylene amino substituent.

Another aspect of this invention relates to a class of compounds of Formula I

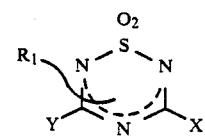

wherein:
$R_1$ is H, alkyl, cycloalkyl, aralkyl or heterocyclylalkyl;
X and Y are each independently halo, hydroxy, alkyl, aryl, alkoxy, mercaptyl, aryloxy, alkylmercaptyl, alkoxyalkyl, hydroxyalkyl, aralkyl, aryloxyalkyl, bicyclic etheralkyl, bicyclic alkylene thioetheralkyl, N-(bicyclic ether or bicyclic alkylene thioether)alkylene amino and amino;

provided that at least one of X or Y is bicyclic ether alkyl, bicyclic alkyl thioether alkyl, N-(bicyclic ether or bicyclic alkylene thioether)alkylene amino;

or a pharmaceutically acceptable salt thereof.

Compounds within the scope of Formula I exhibit physiological activity in mammals including anti-secretory activity, histamine $H_2$-receptor antagonist activity, anti-ulcer activity and cytoprotective activity.

DETAILED DESCRIPTION OF THE INVENTION

A preferred class of compounds according to this invention is described by Formula II:

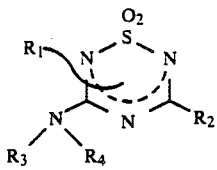

wherein:
$R_1$ is H, lower alkyl, cycloloweralkyl, aryl lower alkyl or heterocyclyl lower alkyl; $R_2$ is —(CH$_2$)$_m$—Z—(CH$_2$)$_n$—B, NR$_5$R$_6$, lower alkyl, aryl, aryl lower alkyl, lower alkoxy, aryloxy, aryloxy lower alkyl, hydroxy lower alkyl, lower alkoxy lower alkyl, halo, hydroxy, mercapto or lower alkyl mercapto;

$R_3$ is H or lower alkyl;

$R_4$ is H, lower alkyl, aryl, aryl lower alkyl, aryloxy lower alkyl or —(CH$_2$)$_m$—Z—(CH$_2$)$_n$—B;

$R_5$ and $R_6$ are each independently H, lower alkyl, aryl, lower alkanoyl, carbamoyl, lower alkyl carbamoyl, amidino, or —(CH$_2$)$_m$—Z—(CH$_2$)$_n$—B;

Z is oxygen or sulfur;

m and n are 0, 1, 2, 3 or 4, provided that m+n≠0; and

B is bicyclic aryl, bicyclic heteroaryl, alkyl bicyclic heteroaryl, bicyclic tetrahydroaryl, bicyclic heterotetrahydroaryl or alkyl bicyclic heterotetrahydroaryl, and bicyclic aryl, bicyclic heteroaryl, bicyclic tetrahydroaryl and bicyclic heterotetrahydroaryl substituted by amino, amino lower alkyl, lower alkylamino, dilower alkylamino, lower alkylamino lower alkyl, dilower alkylamino lower alkyl, guanidino, azaheterocyclyl lower alkyl, or azaheterocyclyl; provided that at least one of $R_2$, $R_4$, $R_5$ and $R_6$ is —(CH$_2$)$_m$—Z—(CH$_2$)$_n$—B;

or a pharmaceutically acceptable salt thereof.

It should be understood that the $R_1$ substituent defined in Formulae I and II may form a chemical bond to the 2, 4 or 6 nitrogen atom of the thiatriazine ring, which substitution pattern can also be described by Formula III, IV and V below.

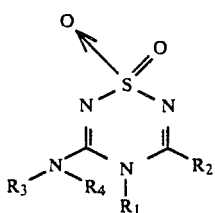

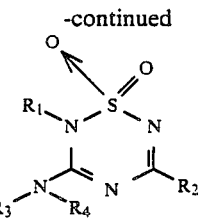

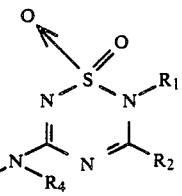

A most preferred class of compounds according to Formula II comprises compounds wherein:
$R_1$ is H, lower alkyl, cycloloweralkyl or aryl lower alkyl;
$R_2$ is amino, lower alkylamino, dilower alkylamino, or lower alkoxy;
$R_3$ is hydrogen; and
$R_4$ is —(CH$_2$)$_m$—Z—(CH$_2$)$_n$—B.

A particularly preferred class of B substituents comprises the following bicyclic groups:

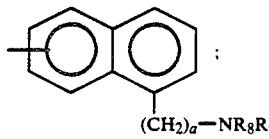

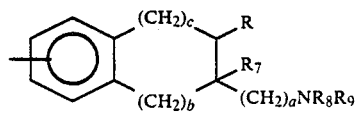

wherein:
a is 0, 1 or 2;
b is 0 or 1;
c is 0, 1, 2 or 3;
R and $R_7$ are each independently H, lower alkyl, allyl, or lower alkyl substituted by aryl, diloweralkylamino or heterocycle;
$R_8$ and $R_9$ are each independently H, lower alkyl, or amidino; or
$R_8$ and $R_9$ together are lower alkylene and together with the nitrogen atom to which they are attached form a 5, 6, or 7 member ring heterocycle which may include one or more additional heteroatoms of N, O or S.

A special embodiment of compounds according to Formula III, IV and V comprises the class wherein:

$R_1$ is H, lower alkyl, cycloloweralkyl or phenyl lower alkyl;

$R_2$ is $NH_2$;

$R_3$ is H or lower alkyl; and $R_4$ is bicyclic benzenoid alkylene ether group of the formula

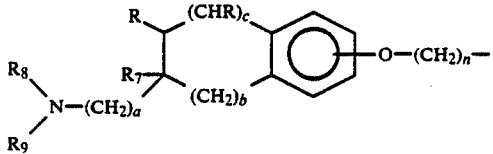

wherein:

a, b and c are 0, 1 or 2;

n is 2, 3 or 4;

R, $R_7$, $R_8$ and $R_9$ are each independently H or lower alkyl or lower alkenyl; or $R_8$ and $R_9$ together are lower alkylene and form with the nitrogen to which they are attached a 5, 6 or 7 member ring heterocycle which may contain one or two additional hetero atoms which may be N, O or S.

A particularly preferred subclass of the foregoing special embodiment comprises the class wherein:

a is 0 or 1;

b is 0;

c is 0, 1, 2 or 3;

n is 3 or 4;

$R_1$ is lower alkyl, cycloloweralkyl or benzyl;

$R_3$ is H; and $NR_8R_9$ is 1-piperidinyl, 1-pyrrolidinyl or 1-morpholinyl.

The compounds of Formulae I and II may also form hydrates and exhibit tautomerism, and the above Formulae are intended to encompass all hydrates and tautomers, as well as any diastereomers and optical enantiomers. A class of compounds of particular interest comprises the class of S(+) optical enantiomers of said particular preferred subclass, wherein the carbon atom to which the $R_7$ group is attached possesses the S(+) absolute configuration.

As employed above and throughout the disclosure, the following terms, unless otherwise indicated, shall be understood to have the following meanings:

"Alkyl" means an aliphatic group. "Lower alkyl" is an alkyl group having 1 to about 6 carbon atoms and is preferred. Examples of lower alkyl groups are methyl, ethyl, n-propyl, isopropyl, butyl, sec-butyl, tert-butyl, n-pentyl, isopentyl, neopentyl and n-hexyl.

"Cycloalkyl" means a cyclic aliphatic group. "Cycloloweralkyl" groups are preferred and comprise about 3 to about 7 carbon atoms.

"Heterocycle" means a hetero atom-containing ring. Preferred heterocycles in the context of the present invention are azaheterocycles of the formula

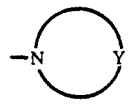

where Y is alkylene or alkylidenyl having from one to six carbon atoms, and may include one to three atoms of N, O or S. Exemplary azaheterocycles include piperidinyl, pyrrolidinyl, morpholinyl, azepinyl, pyrrolyl, imidazolyl, pyrazolyl, and thiamorpholinyl.

"Heteroaryl" means a five or six membered monocyclic aromatic ring which may contain one or more heteroatoms of nitrogen, oxygen or sulfur, including furyl, pyridyl, thiazolyl, imidizolyl, oxazolyl, isooxazolyl, isothiazolyl or thienyl.

"Aryl" means an aromatic hydrocarbon radical group such as phenyl or tolyl, and includes phenyl or tolyl substituted by one or more substituent groups including lower alkyl, halo, carboxyl, amino, lower alkylamino, amido, hydroxyl, nitro, cyano, or lower alkylsulfonyl. Phenyl and tolyl are preferred aryl groups.

"Bicyclic aryl or bicyclic heteroaryl" means a fused bicyclic radical group such as naphthyl, indanyl, quinolinyl or isoquinolinyl.

"Bicyclic tetrahydroaryl or bicyclic tetrahydroheteroaryl" means a fused tetrahydro bicyclic radical group such as tetrahydronaphthyl, tetrahydroquinolinyl or tetrahydroisoquinolinyl.

"Amine substituent" means a radical group of the formula $-NR_3R_4$ wherein $R_3$ and $R_4$ are as defined above.

Compounds of this invention may be prepared according to the exemplary means described below and by analogous means known to those skilled in the art.

The preparation of exemplary B radicals is described in copending U.S. Application Ser. Nos. 489,702, 489,814, 604,813, and 664,222, and PCT Appl. Ser. No. PCT/US84/00657, filed July 27, 1984, and Ser. No. 06/798,697, filed 11/1/85, now U.S. Pat. No. 4,639,442, filed as a PCT application in the U.S. Receiving Office on the same day as the present application (all assigned to the assignee of the present application) the disclosures of which are hereby incorporated by reference.

The compounds of the present invention may be prepared by reacting an appropriately substituted thiatriazine moiety of Formula VI with an amine such as $B-(CH_2)_n-X-(CH_2)_m-NH_2$. Scheme I below depicts a typical reaction sequence.

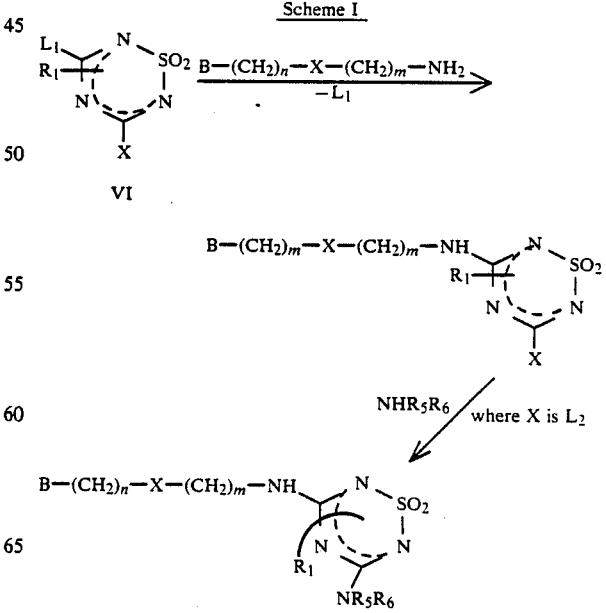

The amine substituent groups displace the leaving group designated $L_1$ in Formula V, which can be any group which is displaced preferentially over the X substituent group such as for example a para-nitrophenoxy substituent. When X in Scheme I is other than amine and a second amine substituent is desired, then X is a less preferential leaving group designated $L_2$ in Scheme I above such as methoxy. Treatment with a nucleophilic amine displaces the methoxy group.

The starting thiatriazine compounds of Formula V are readily prepared according to methods known in the art. One method for preparing the thiatriazines is described in Scheme II below.

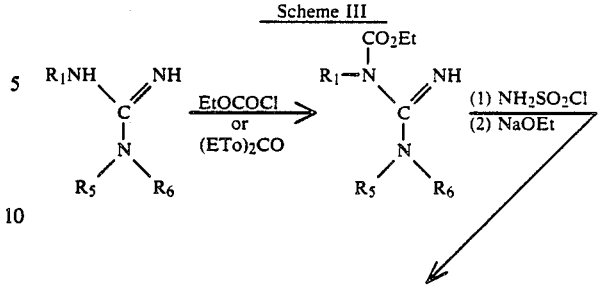

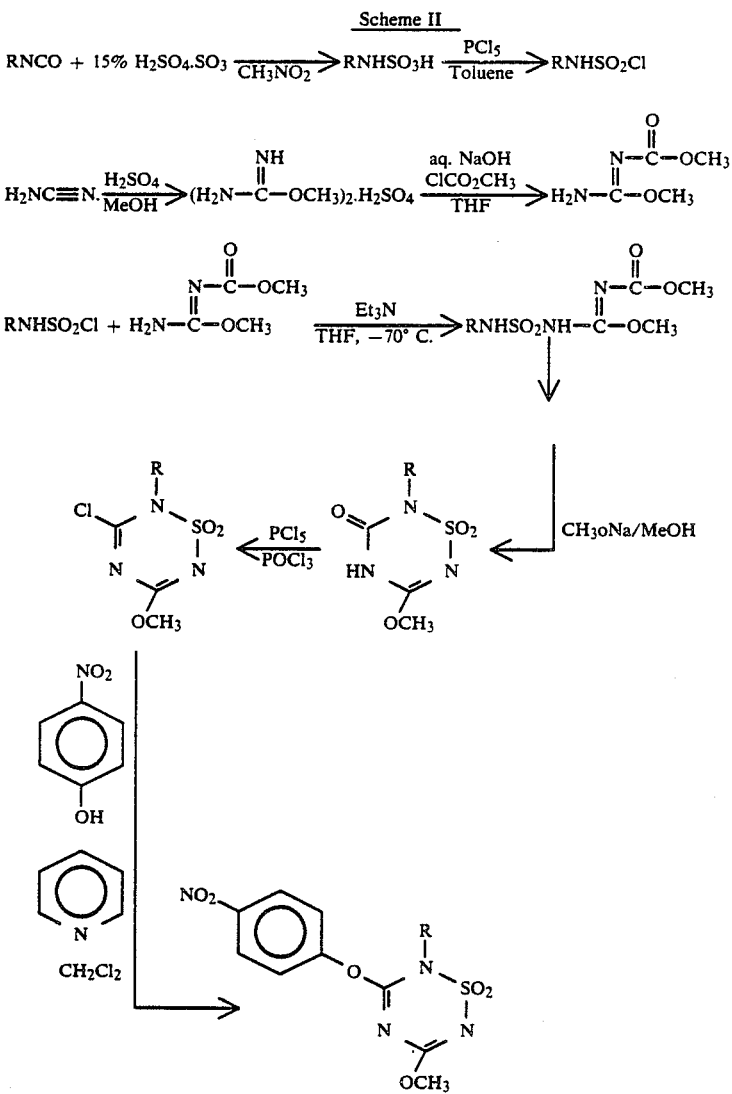

The thiatriazine intermediates may also be prepared according to methods disclosed in U.S. Pat. Nos. 4,013,447, 4,343,648, and 4,426,219, hereby incorporated by reference. Scheme II depicts a typical reaction sequence.

Using a suitable N-substituted guanadine derivative as starting material, the guanadine is N-acylated with ethyl chloro formate on the $R_1$ substituted nitrogen. The remaining unsubstituted nitrogen is N-sulfonated with amino sulfonyl chloride and the resulting addition product cyclized to the 4-$R_1$-3-oxo-thiatriazine by treatment with anhydrous alkoxide.

The 4-alkyl, 3-oxo thiatriazine intermediate is then converted into the 3-halo compounds upon treatment with phosphorous pentachloride. A typical reaction is described in U.S. Pat. No. 4,426,219. Treatment of the 3-chloro compound with paranitrophenol results in the 3-paranitrophenoxy-, 4-alkyl-thiatriazine compound.

Another method for producing a 4-alkyl thiatriazine intermediate is described in Scheme IV below.

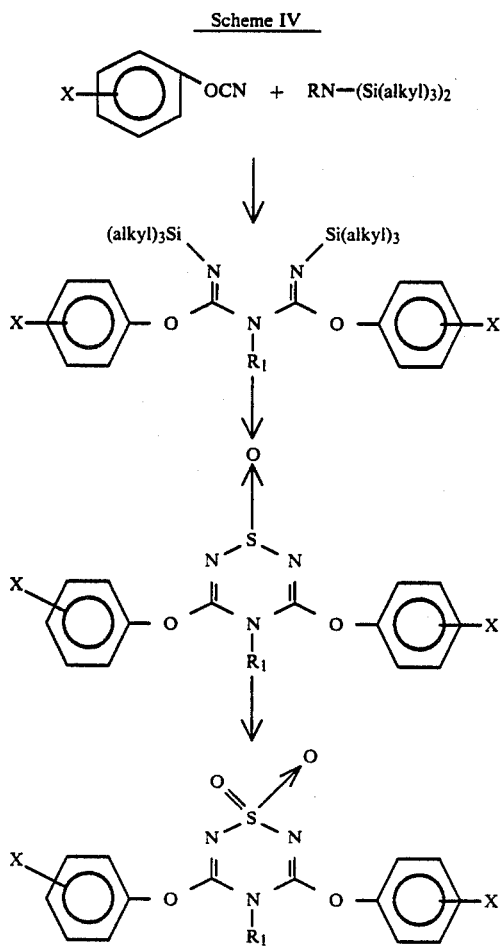

In Scheme IV, an aryl cyanate is reacted with a substituted bis-trialkylsilylamine $R_1$ is as defined above. The trialkyl group is preferably a trimethyl group and may be carried out as described in Chem. Ber. 101 3185 (1968). The thiatriazine may be formed by cyclization with thionyl chloride. The 1,1-dioxide may be formed using an oxidizing agent, for example: a peracid, such as m-chloroperbenzoic acid, hydrogen peroxide; an alkyl hydroperoxide, such as t-butyl hydroperoxide; or a permanganate, such as potassium permanganate.

The 6-substituted thiatriazine compound may be prepared from the 5-amino-B 3-aryloxy-6-substituted 1,2,4,6-thiatriazine-1,1-dioxide reagent, an exemplary preparation of which is described in Scheme V below.

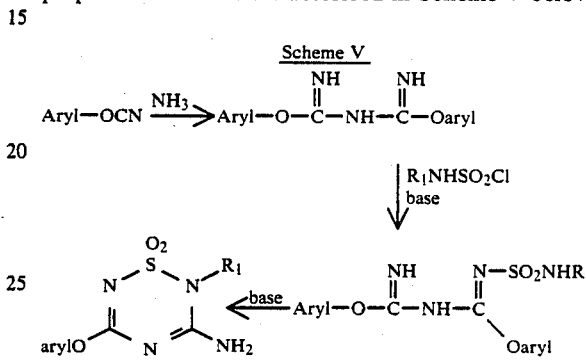

Treatment of an arylcyanate with ammonia gas results in the formation of the dimeric addition product which can be N-sulfonated with an $R_1$ substituted sulfonyl halide in the presence of a non-nucleophilic scavenger base. See, E. Grigat and R. Putter, Chem. Ber., 97, 3207 (1964). Treatment of the N-sulfo product with a base, such as a hydride base, for example sodium hydride, results in cyclization to the 6-$R_1$ substituted 1,2,4,6-thiatriazine which can then be reacted with the N-(bicyclic ether or bicyclic alkylene thioether)alkylene amine intermediate resulting in the desired 6-substituted thiatriazine compounds of Formula I.

Compounds of Formula I wherein one of X or Y is aryloxyalkyl, alkoxyalkyl, aralkyl, alkyl or aryl may be prepared by the reaction sequence shown in Scheme VI below.

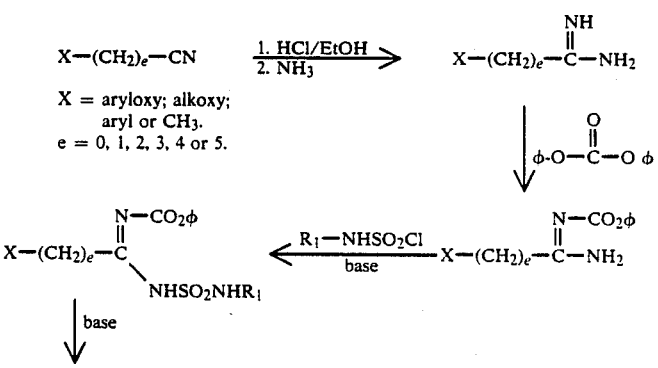

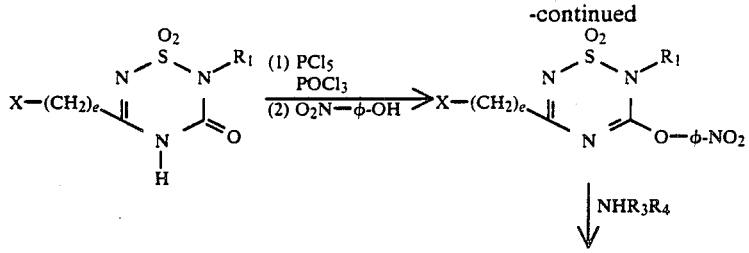

-continued

Treatment of the cyano starting material with ethonolic acid followed by ammonia results in an amidine which is N-acylated with any appropriate formate ester acylating agent to form the N-carbo phenoxylate adduct. N-sulfonation of the primary amine group in the presence of a scavenger base, such as triethylamine, forms the N-carbophenoxy, N'-R$_1$-sulfonamide adduct, which upon treatment with base, such as a hydride (NaH), cyclizes to the 5-oxo-1,2,4,6-thiatriazine-1,1-dioxide intermediate. Conversion of the 5-oxo intermediate to the p-nitrophenoxy reagent by means of the chloride is effected as described above. The p-nitrophenoxy group is displaceable by treatment with the N-(bicyclic) amine, NHR$_3$R$_4$, thereby forming the corresponding compound within the scope of Formula I.

This invention also relates to a novel method and intermediates useful in the preparation of 4-substituted thiatriazine compounds of Formula I.

The process according to the present invention comprises the formation of a 3-amino-4-R-5-(aryloxy)-1,2,4,6-thiatriazine-1,1-dioxde intermediate by reacting an N-cyano-N-[aryloxyimino]isopropylamine with a novel reagent, N-halosulfonyl-trimethylsilylcarbamate. An exemplary reaction sequence is shown in Scheme VII below.

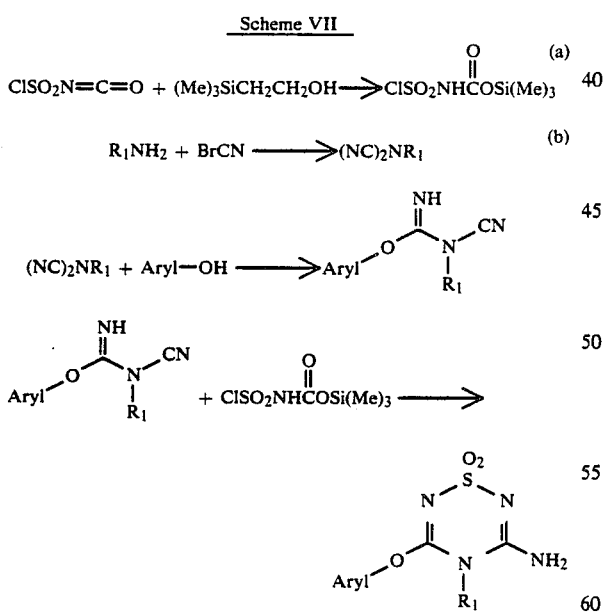

Treatment of the R$_1$ amino compound with an excess of cyanogen halide followed by the further treatment with additional cyanogen halide and base results in an N,N-dicyano-R$_1$-amine (see, P. H. Benders and J. T. Hackman, *Recueil Chim. Phys. Bas.*, 91, 343 (1972)) which reacts with a hydroxyl reagent to form the N-cyano-N-oxyimino amine (see, P. H. Benders, J. Royal Netherlands Chem. Soc., 95 (9) 217 (1976)). Reaction of two moles of the amine with one mole of the halosulfonyl-trimethylsilylcarbamate results in the 4-R$_1$-substituted thiatriazine.

The silylcarbamate is prepared by reacting trimethylsilylethanol with halosulfonylisocyanate. The reaction proceeds by the rearrangement of the urethane adduct with evolution of ethylene. The silylcarbamate is isolated in substantially quantitive yield and is used preferably immediately in the subsequent reaction steps.

A modification of the above reaction sequence may also be used to prepare the 6-R$_1$ substituted thiatriazine compounds of Formula I. Reaction of a cyano-aryl ether with NH$_2$CN forms the N-cyano-N-aryloxyamino-amine compound which, when treated with a halosulfonyl-R$_1$-amine such as ClSO$_2$NHR$_1$, cyclizes to form the 6-R$_1$ thiatriazine as shown in Scheme VIII below.

Scheme VIII

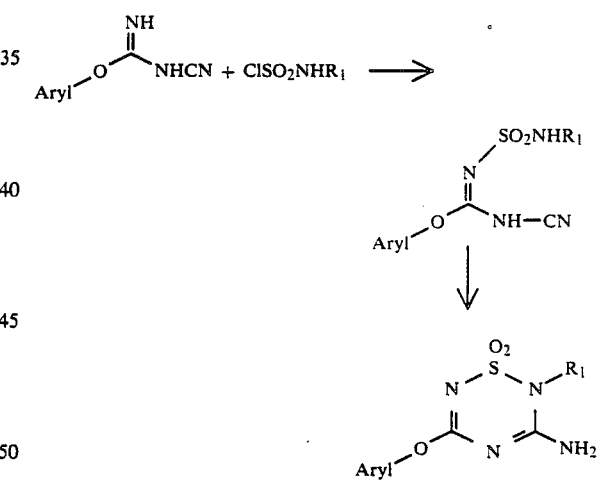

The following are selected examples of the preparation of compounds according to this invention which utilize starting materials which are either commercially available, prepared according to methods known in the art or described in the above references, and are hereby incorporated by reference.

EXAMPLE 1

The Preparation of 5-Amino-2-Benzyl-3-[3-[5-[1-(1-Piperidinyl)-1,2,3,4-Tetrahydronaphthyloxy]]Propylamino]-2H-1,2,4,6-Thiatriazine-1,1-Dioxide Step 1. Benzylsulfamic acid Benzylisocyanate (13.3 g) is added dropwise to a stirred mixture of nitromethane (160 ml) and 15% fuming sulfuric acid (5.4 ml) at about 10° C. The reaction mixture is refluxed for about one hour, cooled to RT and the solid filtered and washed with nitromethene. The solid is suspended in ether, filtered, dried and used as a crude solid in the next step.

Step 2. Benzylsulfamoyl chloride

A stirred mixture of benzylsulfamic acid (73 g), PCl$_5$ (81 g) in toluene (540 ml) is heated to 40°–50° C. for one hour and refluxed for about 3 hours. The cooled mixture is filtered through Celite and the filtrate concentrated in vacuo to remove the toluene affording the desired product as a liquid.

Step 3. N-carbomethoxy-N'-benzylsulfamyl-O-methylisourea

A solution of benzylsulfamoyl chloride (168 g) in anhydrous THF (300 ml) is added dropwise to a stirred solution of N-carbomethoxy-O-methylisourea (107 g) and triethylamine (90 g) in anhydrous THF (800 ml) under nitrogen at −70° C. The resulting suspension is warmed to RT, filtered and the filtrate evaporated in vacuo. The residue is partitioned between methylene chloride and 0.5N aq. HCl. The organic layer is dried, filtered, and concentrated in vacuo affording the desired product as an oil.

Step 4. 2-Benzyl-5-methoxy-2H-1,2,4,6-thiatriazin-3-one-1,1-dioxide

A solution of N-carbomethoxy-N'-benzylsulfamoyl-O-methylisourea (215 g) in anhydrous THF (200 ml) is added dropwise to a stirred suspension of sodium hydride (43 g of 60% dispersion) in anhydrous THF (900 ml) and refluxed for 2 hours under nitrogen. Water (800 ml) is added to the cooled reaction mixture and the aqueous mixture washed with ether. The pH of the aqueous layer is adjusted to about 3.2 and the resulting suspension extracted with methylene chloride. The methylene chloride extract is dried, filtered, and evaporated in vacuo. The residue is taken up in hot isopropyl alcohol, treated with charcoal, filtered hot, concentrated, cooled, the resulting precipitate filtered and dried in vacuo yielding the desired product, M.P.=141°–144° C.

Step 5. 2-Benzyl-3-chloro-5-methoxy-2H-1,2,4,6-thiatriazine-1,1-dioxide

A stirred mixture of 2-benzyl-5-methoxy-2H-1,2,4,6-thiatriazin-3-one-1,1-dioxide (10.5 g) and PCl$_5$ (12.2 g) in POCl$_3$ (35 ml) is refluxed overnight. The reaction mixture is evaporated in vacuo at 50° C. affording the crude product as an oil.

Step 6. 2-Benzyl-5-methoxy-3-p-nitrophenoxy-2H-1,2,4,6-thiatriazine-1,1-dioxide

A solution of 2-benzyl-3-chloro-5-methoxy-2H-1,2,4,6-thiatriazine-1,1-dioxide (3.8 g) in methylene chloride (10 ml) is added dropwise to a stirred mixture of p-nitrophenol (1.7 g) and pyridine (2.4 g) in methylene chloride (20 ml). The reaction mixture is heated to reflux for 3 hours, cooled, washed with 3N aq. HCl and sat'd aq. Na$_2$CO$_3$. The methylene chloride layer is dried, filtered and evaporated in vacuo yielding the desired product as an oil.

Step 7. 2-Benzyl-5-methoxy-3-[3-[5-[1-(1-piperidinyl)-1,2,3,4-tetrahydronaphthyloxy]propylamino]-2H-1,2,4,6-thiatriazine-1,1-dioxide A solution of 2-benzyl-5-methoxy-3-p-nitrophenoxy-2H-1,2,4,6-thiatriazine-1,1-dioxide (7.8 g) and triethylamine (3.5 g) in methylene chloride (50 ml) is added to a stirred solution of 5-(3-aminopropoxy)-1-(1-piperidinyl)-1,2,3,4-tetrahydronaphthalene (10.5 g) in methylene chloride (75 ml) and the reaction mixture stirred at RT for about 16 hours. The reaction mixture is washed with sat'd aq. Na$_2$CO$_3$ and the organic layer dried, filtered and the filtrate evaporated in vacuo. The residue is chromatographed on silica gel (36 g) eluting with ethyl acetate. The purified fractions are combined and evaporated yielding the desired product as an oil which is used in the next step.

Step 8. 5-Amino-2-benzyl-3-[3-[5-[1-(1-piperidinyl)-1,2,3,4-tetrahydronaphthyloxy]]propylamino]-2H-1,2,4,6-thiatriazine-1,1-dioxide Liquid ammonia (30 ml) is added to a bomb containing a stirred solution of the 2-benzyl-5-methoxy compound of Step 8 above (11.6 g) in methanol (150 ml) cooled in a dry ice/acetone bath. The bomb is sealed and stirred at 75°–80° C. for about 60 hours. The reaction mixture is evaporated and the residue taken up in hot isopropyl alcohol, treated with charcoal, filtered hot and the filtrate concentrated. The resulting precipitate is filtered and washed with isopropyl alcohol yielding the desired product, M.P.=179°–180° C.

EXAMPLE 2

The Preparation of 2-n-Butyl-5-Methoxy-3-[3-[5-[1-(1-Piperidinyl)-1,2,3,4-Tetrahydronaphthyloxy]]-Propylamino]-2H-1,2,4,6-Thiatriazine-1,1-Dioxide Step 1. 2-n-Butyl-5-methoxy-3-p-nitrophenoxy-2H-1,2,3,4,6-thiatriazine-1,1-dioxide A solution of 2-n-butyl-3-chloro-5-methoxy-2H-1,2,4,6-thiatriazine-1,1-dioxide (38 g) in methylene chloride (250 ml) is added dropwise to a stirred mixture of p-nitrophenol (28 g) and triethylamine (41 g) in methylene chloride (230 ml). The reaction mixture is refluxed for about 3.5 hours, cooled and partitioned between sat'd aq. Na$_2$CO$_3$ and methylene chloride. The methylene chloride layer is separated, washed, dried and concentrated. The residue is dissolved in isopropyl acetate, treated with charcoal, filtered and the filtrate concentrated and cooled. The resulting precipitate is filtered and the filtrate concentrated to an oil which is chromatographed on silica gel using methylene chloride as eluent. The pure fractions are combined, concentrated and crystallized from ether yielding the desired p-nitrophenoxy product as a solid, M.P.=52°–55° C.

Step 2. 3-Amino-2-n-butyl-5-methoxy-2H-1,2,4,6-thiatriazine-1,1-dioxide

Ammonia gas is bubbled for about 25 min., into a stirred solution of 2-n-butyl-5-methoxy-3-p-nitrophenoxy-2H-1,2,4,6-thiatriazine-1,1-dioxide (9.2 g) in methylene chloride (125 ml) cooled in a methanolic ice bath. The reaction mixture is allowed to warm to RT and excess ammonia is evaporated. The reaction mixture is partitioned between 5% aq. NaOH and methylene chloride and the aqueous layer separated and acidified to about pH 9. The resulting precipitate is filtered and the filtrate extracted with methylene chloride and dried. The methylene chloride extract is evaporated and the solids are combined and recrystallized from hot toluene yielding the desired 3-amino product as a solid, M.P. 152°–153° C.

Step 3. 2-n-Butyl-5-methoxy-3-[3-[5-[1-(1-piperidinyl)-1,2,3,4-tetrahydronaphthyloxy]]propylamino]-2H-1,2,4,6-thiatriazine-1,1-dioxide A solution of the p-nitrophenoxy compound from Step 1 above in methylene chloride (60 ml) is added dropwise to a stirred mixture of 5-[3-aminopropoxy]-1-(1-piperidinyl)-1,2,3,4-tetrahydronaphthalene (8.7 g) and triethylamine (4 g) in methylene chloride (90 ml).

The reaction mixture is stirred at RT for 4 hours and extracted with aq. sat'd Na₂CO₃. The methylene chloride fraction is dried, filtered and concentrated yielding the desired product as an oil.

EXAMPLE 3

The Preparation of 5-Amino-2-n-Butyl-3-[3-[5-[1-Piperidinyl)-1,2,3,4-Tetrahydronaphthyloxy]]Propylamino]2H-1,2,4,6-Thiatriazine-1,1-Dioxide Liquid ammonia (15–20 ml) is added to a solution of the 2-n-butyl-5-methoxy compound of Example 2 above (19 g) in methanol (80 ml) stirred in a bomb cooled in a dry ice/acetone bath. The bomb is sealed and heated at 60°–90° C. for about two days. The reaction mixture is cooled and concentrated in vacuo and the residue chromatographed on silica gel (300 g) (eluent=CH₂Cl₂ and 1% MeOH/CH₂Cl₂). The purified fractions are combined, concentrated in vacuo and dissolved in methanol. Methanesulfonic acid (1.4 g) is added to the solution and the solution evaporated in vacuo forming a white foam which is dissolved in water. The aqueous solution is washed with ethyl acetate, basified to pH 9–10 and extracted with methylene chloride. The organic extract is dried, filtered and the solvent evaporated to yield the desired product as a foam, M.P.=70°–80° C.; (Tartrate isopropanolate, M.P.=110° C. (dec)).

EXAMPLE 4

The Preparation of 5-Methoxy-2-Methyl-3-[3-(5-[1-(1-Piperidinyl)-1,2,3,4-Tetrahydronaphthyloxy])Propylamino]-2H-1,2,4,6-Thiatriazine-1,1-Dioxide Step 1. 5-Methoxy-2-methyl-3-p-nitrophenoxy-2H-1,2,4,6-thiatriazine-1,1-dioxide A solution of 3-chloro-5-methoxy-2-methyl-2H-1,2,4,6-thiatriazine-1,1-dioxide (48 g) in methylene chloride (25.5 ml) is added dropwise to a stirred mixture of p-nitrophenol (38 g) and triethylamine (55 g) in methylene chloride (1 l). The mixture is stirred at RT for about 12 hours, refluxed for about 3½ hours, concentrated in vacuo, the residue is treated with sat'd aq. Na₂CO₃ solution, and the resulting insoluble solid filtered and washed with water and CH₂Cl₂. The solid is recrystallized from ethyl acetate/acetonitrile yielding the p-nitrophenoxy compound as a crystalline solid, M.P.=220°–221° C.

Step 2. 5-Methoxy-2-methyl-3-[3-(5-[1-(1-piperidinyl)-1,2,3,4-tetrahydronaphthyloxy])propylamino]-2H-1,2,4,6-thiatriazine-1,1-dioxide A suspension of 5-methoxy-2-methyl-3-p-nitrophenoxy-2H-1,2,4,6-thiatriazine-1,1-dioxide (9.4 g) in methylene chloride is added to a stirred mixture of 5-)3-aminopropoxy)-1-(1-piperidinyl)-1,2,3,4-tetrahydronaphthalene (8.7 g) and triethylamine (4.0 g) in methylene chloride (90 ml). The reaction mixture is stirred for about 12 hours at RT, extracted with sat'd aq. Na₂CO₃ and the methylene chloride layer dried, filtered and concentrated in vacuo yielding the desired product as an oil.

EXAMPLE 5

The Preparation of 5-Amino-2-Methyl-3-[3-[5-[1-(1-Piperidinyl)-1,2,3,4-Tetrahydronaphthyloxy]]Propylamino]-2H-1,2,4,6-Thiatriazine-1,1-Dioxide Liquid ammonia (15–20 m) is added to a stirred solution of the compound of Example 4 above (13 g) in methanol (100 ml), cooled to dry ice/acetone bath temperatures in a bomb. The bomb is sealed and warmed to 90° C. and kept at 90° C. for about 70 hours. The reaction mixture is cooled to RT, and the insoluble solid is filtered, and washed with methanol and the filtrate evaporated. The solid is twice recrystallized from hot ethanol, and once from a mixture of hot 95% EtOH and methanol, yielding the desired product as a white crystalline solid, M.P. 242°–244° C.

EXAMPLE 6

The Preparation of 4-Methyl-5-(3-Methylphenoxy)-3-[3-[5-[1-(1-Piperidinyl)-1,2,3,4-Tetrahydronaphthyloxy]]-Propylamino]-1,2,4,6-Thiatriazine-1,1-Dioxide Step 1. 4-Methyl-3,5-(3-methylpheoxy)-1,2,4,6-thiatriazine-1-oxide 8.8 g of bis(trimethylsilyl)methylamine are added to 13.3 g of 3-methylphenylcyanate stirred neat under nitrogen cooled with an ice and water bath. The reaction mixture is kept at RT for about 42 hours. The resulting oil is decanted from the solid precipitate, dissolved in methylene chloride, and cooled to about −10° C. Thionyl chloride (2 ml) is added dropwise to the stirred mixture while maintaining a temperature less than about 0° C. and stirred for one hour at 5° C. Ice water is added to the reaction mixture and the organic phase separated, washed with water, dried, evaporated and the resulting oil recrystallized with ether affording the desired product as a white solid, M.P. 126°–129° C.

Step 2. 4-Methyl-3,5-bis-(3-methylphenoxy)-1,2,4,6-thiatriazine-1,1-dioxide

A solution of m-chloroperbenzoic acid (4.7 g) in chloroform (30 ml) is added at RT to a stirred solution of 4-methyl-3,5-bis-(3-methylphenoxy)1,2,4,6-thiatriazine-1-oxide (3.1 g) in chloroform (15 ml). The reaction mixture is refluxed for about 5 minutes and the precipitate taken up in methylene chloride, washed with sat'd aq. Na₂CO₃, brine, dried, filtered and evaporated to a solid. The solid is recrystallized from isopropyl acetate using charcoal, affording the desired product, M.P. 221°–223° C.

Step 3. 4-Methyl-5-(4-methoxyphenoxy)-3-[3-5-(1-piperidinyl)-1,2,3,4-tetrahydronaphthyloxy]]-propylamino]-1,2,4,6-thiatriazine-1,1-dioxide A solution of 4-methyl-3,5-bis(4-methylphenoxy)-1,2,4,6-thiatriazine-1,1-dioxide (10.8 g) in methylene chloride (50 ml) is added to a stirred solution of 5-(3-aminopropoxy)-1-(1-piperidinyl)-1,2,3,4-tetrahydronaphthalene (3.7 g) and triethylamine (4.0 g) in methylene chloride (100 ml). The reaction mixture is stirred at RT overnight, evaporated and chromatographed on silica gel (eluent CH₃OH) affords an oil which is triturated with ether affording a precipitate which is filtered and dried in vacuo, affording the desired compound M.P. 122° C.

EXAMPLE 7

The Preparation of
5-Amino-4-Methyl-3-[3-[5-[1-(1-Piperidinyl)-1,2,3,4-Tetrahydronaphthyloxy]]Propylamino]-1,2,4,6-Thiatriazine-1,1-Dioxide 40 ml of condensed ammonia is poured into a solution of the 5-methylphenoxy compound of Example 6 above (12.6 g) in methanol (200 ml) in a bomb at dry ice/acetone bath temperature. The bomb is sealed and heated to 90° C. for about 48 hours. The reaction mixture is evaporated, triturated with ether and the precipitate taken up in hot methanol and chromatographed on silica gel removing all faster moving components eluting with methanol. The insoluble material is taken off the column and recrystallized from DMSO and H₂O, affording the desired product as a pink solid, M.P. >250° C.

EXAMPLE 8

The Preparation of
5-Methoxy-2-Isopropyl-3-[3-[5-[1-(1-Piperidinyl)-1,2,3,4-Tetrahydronaphthaloxy]]Propylamino]-2H-1,2,4,6-Thiatriazine-1,1-Dioxide A solution of 2-isopropyl-5-methoxy-2-(4-nitrophenoxy)-2H-1,2,4,6-thiatriazine-1,1-dioxide (5.87 g) in CH₂Cl₂ (40 ml) is added dropwise to a stirred solution of 5-[3-aminopropoxy]-1-(1-piperidinyl)-1,2,3,4-tetrahydronaphthalene (4.9 g) and triethylamine (2.2 g) in CH₂Cl₂ (80 ml). The reaction mixture is stirred overnight, washed with the aq. HCl (3N), water and sat'd aq. Na₂CO₃, dried, filtered and evaporated to a foam. The foam is dissolved in methylene chloride and flash chromatographed (silica gel, 300 g) eluting with EtOAC/CH₂Cl₂. The pure fractions are evaporated yielding the desired product as a yellow oil.

EXAMPLE 9

The Preparation of
5-Amino-2-Isopropyl-3-[3-[5-[1-(1-Piperidinyl)-1,2,3,4-Tetrahydronaphthaloxy]]Propylamino]-2H-1,2,4,6-Thiatriazine-1,1-Dioxide A solution of the oil obtained in Example 8 in MeOH (60 ml) is stirred in a bomb cooled in a dry ice/acetone bath. Condensed ammonia (15 ml) is added to the bomb which is sealed, warmed to RT, and heated at 90° C. for two days. The reaction mixture is evaporated and the resulting oil dissolved in EtOAC which is extracted with aqueous acid. The acid layer is basified to pH 8–9, extracted with methylene chloride, washed with sat'd Na₂CO₃, dried, filtered and evaporated. The resulting oil is flash chromatographed (silica gel, 180 g) eluting with EtOAC and the combined pure fractions are evaporated and crystallized from diethyl ether affording the desired product, M.P.=142°–146° C.

EXAMPLE 10

The Preparation of
5-Amino-2-Cyclohexyl-3-[3-[5-[1-(1-Piperidinyl)-1,2,3,4-Tetrahydronaphthaloxy]]Propylamino]-1H-1,2,4,6-Thiatriazine-1,1-Dioxide Step 1. 5-Methoxy-2-cyclohexyl-3-[3-[5-[(1-piperidinyl)-1,2,3,4-tetrahydronaphthaloxy]]-propylamino]-2H-1,2,4,6-thiatriazine-1,1-dioxide A solution of 2-cyclohexyl-5-methoxy-3-paranitrophenoxy-1,2,4,6-thiatriazine-1,1-dioxide/mono tetrahydro furanate (9.1 g) in methylene chloride (50 ml) is added dropwise to a stirred solution of 5-(3-aminopropoxy)-1-(1-piperidinyl)-1,2,3,4-tetrahydronaphthalene (5.8 g) in methylene chloride (80 ml). The reaction mixture is stirred overnight at RT, washed with aq. HCl, water, sat'd aq. Na₂CO₃, dried, filtered and evaporated to an orange oil. The residue is chromatographed on a silica gel column (400 g) eluting with methylene chloride and increasing concentrations of ethyl acetate and the purified fractions combined and evaporated to a foam which is determined by NMR analysis to be the desired product.

Step 2. 5-Amino-2-cyclohexyl-3-[3-[5-[(1-piperidinyl)-1,2,3,4-tetrahydronaphthaloxy]]propylamino]-2H-1,2,4,6-thiatriazine-1,1-dioxide Condensed ammonia (25 ml) is added to a stirred methanolic solution of the compound prepared in Step 1. (8.3 g in methanol 100 ml) in a bomb cooled in a dry ice/acetone bath. The bomb is sealed, warmed to RT and heated to 95° C. for two days. The reaction mixture is cooled in a dry ice/acetone bath, and the cooled mixture evaporated and dissolved in ethyl acetate. The solution is extracted with aqueous acid and the acidic layer made basic with sat'd aq. Na₂CO₃. The basic solution is extracted with methylene chloride, and the organic extract washed with aqueous base, dried, filtered and evaporated to an oil. The oil is chromatographed on silica gel eluting with ethyl acetate. The purified fractions are combined, evaporated and stirred with ether resulting in a white precipitated which is filtered and dried affording the desired product, M.P. 149°–152° C.

When intermediates such as 3- or 5-[3-aminopropoxy]benzocyclobutenes are utilized in reaction sequences analogous to those described above, the analogous benzocyclobutene thiatriazine adducts are obtained. An exemplary compound is 5-amino-2-cyclohexyl-3-[5-[1-allyl-1-(1-piperidinylmethyl)benzocyclobutenyloxy]]-propylamino]-2H-1,2,4,6-thiatriazine-1,1-dioxide malic acid salt, M.P.=73°–75° C. (dec).

EXAMPLE 11

The Preparation of
5-Amino-4-Methyl-3-[3-[4-[1-(1-Piperidinyl)Indanyloxy]]Propylamino]-2H-1,2,4,6-Thiatriazine-1,1-Dioxide Step 1. 4-Methyl-5-(3-methyl)phenoxy-3-[3-[4-[(1-piperidinyl)indanyloxy]]propylamino]-2H-1,2,4,6-thiatriazine-1,1-dioxide A solution of 3,5-bis(3-methylphenoxy)-4-methyl-2H-1,2,4,6-thiatriazine-1,1-dioxide (5.4 g) in methylene chloride (25 ml) is added to a stirred solution of 4-(3-aminopropoxy)-1-(1-piperidinyl)indan (4.1 g) and triethylamine (2.0 g) in methylene chloride (50 ml) and stirred overnight at RT. The reaction mixture is evaporated and the residue triturated with ether. The precipitate is filtered; the filtered solid is washed with ether and dried, affording the desired product.

Step 2. 5-Amino-4-methyl-3-[3-[4-[1-(1-piperidinyl)indanyloxy]]propylamino]-2H-1,2,4,6-thiatriazine-1,1-dioxide A stirred mixture of the 5-(3-methylphenoxy)-3-amino thiatriazine compound of Step 1. above (6.0 g) and condensed ammonia (20 ml) in methanol (25 ml) in a bomb is heated to 90° C. overnight, cooled and evaporated. The residue is stirred in diethyl ether and the solid is filtered. The filtered solid is dissolved in a mixture of ethanol and methanol, and the solution is cooled resulting in a precipitate which is filtered and recrystallized from hot methanol affording the desired product, M.P. >250° C.

EXAMPLE 12

The Preparation of 5-Amino-6-n-Butyl-3-[3-[5-[1-(1-Piperidinyl)-1,2,3,4-Tetrahydronaphthyloxy]]Propylamino]-2H-1,2,4,6-Thiatriazine-1,1Dioxide Step 1. Imino-bis-[(3-methylphenyl)carbimidic acid]

A stream of ammonia gas is passed for one hour over a vigorously stirred solution of 3-methylphenylcyanate (73.5 g) in diethyl ether (250 ml) cooled in a methanolic ice bath. The mixture is filtered and the solid is washed with cold ether. The filtrate is cooled and the resulting precipitate collected and dried affording the desired product, M.P.=98°-99° C.

Step 2. [N-n-butylsulfamoyl]imino-bis-[(3-methylphenyl)carbimide acid]

A solution of n-butylsulfamoyl chloride (0.59 g) in THF (3 ml) is added dropwise to a stirred solution of imino-bis-[(3-methylphenyl)carbimidic acid] (1 g) and triethylamine (0.35 g) in THF (20 ml) and the reaction mixture stirred overnight at RT. The mixture is poured into $H_2O$, extracted with methylene chloride and evaporated to an oil which is flash chromatographed on silica gel (eluent, pet. ether/ethyl acetate). The purified oil crystallizes on standing affording the desired product, M.P.=94°-96° C.

Step 3. 5-Amino-6-n-butyl-3-(3-methylphenoxy)-1,2,4,6-thiatriazine-1,1-dioxide

A solution of the imino bis compound of Step 2. about (4.7 g) in THF (60 ml) is added to a stirred suspension of sodium hydride (from 0.92 g of 60% mineral oil suspension-washed) and the mixture stirred at RT for about 15 min. The mixture is poured into $H_2O$, extracted with diethyl ether, the ethereal layer is dried, filtered and evaporated. Flash chromatography on silica gel affords the purified desired product as a solid, M.P.=169°-171° C.

Step 4. 5-Amino-6-n-butyl-3-[3-[5-[1-(1-piperidinyl)-1,2,3,4-tetrahydronaphthyloxy]]propylamino]-2H-1,2,4,6-thiatriazine-1,1-dioxide A solution of the 3-(3-methylphenoxy)thiatriazine compound of Step 3. above (0.55 g) in methylene chloride (20 ml) is added dropwise to a stirred solution of 5-(3-aminopropoxy)-1-(1-piperidinyl)-1,2,3,4-tetrahydronaphthalene (0.5 g) and triethylamine (0.3 g) in methylene chloride (20 ml) and the mixture stirred at RT overnight. The reaction mixture is extracted with aqueous base, and the organic layer dried and evaporated. The residue is flash chromatographed (silica gel) and the purified fractions combined and recrystallized affording the desired product, M.P.=87°-93° C.

EXAMPLE 13

Analogous compounds, wherein the 6-position of the thiatriazine is substituted by isopropyl or cyclohexyl, may be prepared from analogous precursors, such as, 6-N-(2-propyl)-5-amino-3-(3-methylphenoxy)-1,2,4,6-thiatriazine-1,1-dioxide, M.P.=158°-161° C.; and 6-N-cyclohexyl-5-amino-3-(3-methylphenoxy)-1,2,4,6-thiatriazine-1,1-dioxide, M.P.−216°-217° C.

Examples include the following:

5-Amino-6-n-butyl-3-[3-[4-[1-(1-piperidinyl)-indanyloxy]]propylamino]-2H-1,2,4,6-thiatriazine-1,1-dioxide, M.P.=65°-70° C.

5-Amino-6-cyclohexyl-3-[3-[5-[3-(1-piperidinyl)-1,2,3,4-tetrahydronaphthyloxy]]propylamino]-2H-1,2,4,6-thiatriazine-1,1-dioxide, M.P.=95°-101° C.

5-Amino-6-cyclohexyl-3[3-[4-[1-(1-piperidinyl)indanyloxy]]-propylamino]-2H-1,2,4,6-thiatriazine-1,1-dioxide tartrate, M.P.=145°-150° C.

5-Amino-6-isopropyl-3-[3-[5-[1-(1-piperidinyl)-1,2,3,4-tetrahydronaphthyloxy]]propylamino]-2H-1,2,4,6-thiatriazine-1,1-dioxide tartrate isopropanolate, M.P.=105° C. (dec).

EXAMPLE 14

The Preparation of the Intermediate Compound, 3-p-Nitrophenoxy-2-n-Butyl-5-Phenyl-1,2,4,6-Thiatriazine-1,1-Dioxide Step 1. Benzamidine phenyl carbamate A solution of diphenyl carbonate (13.7 g) in THF (500 ml) is added to a stirred mixture of benzamidine (8 g) in methaol (300 ml) and the mixture is refluxed for about six hours. The mixture is evaporated, diethyl ether added, the precipitate filtered and the filtrate evaporated affording the desired product.

Step 2. N-carbophenoxy-N'-n-butylsulfamoyl benzamidine n-Butylsulfonyl chloride (6.67 g) in THF (50 ml) is added dropwise to a stirred solution of the carbamate compound of Step 1. above (95 g) and triethylamine (4 g) in THF (160 ml) cooled to −78° C. The reaction mixture is warmed to RT, stirred overnight, poured into $H_2O$ and extracted with diethyl ether. The diethyl ether extract is washed, dried, filtered and evaporated, and the residue flash chromatographed (silica gel) affording the desired product in purified form.

Step 3. 2-n-Butyl-3-oxo-5-phenyl-1,2,4,6-thiatriazine-1,1-dioxide

A solution of the benzamidine compound from Step 2. above (0.5 g) in THF (20 ml) is added to a suspension of NaH (110 mg of 60% mineral oil suspension, washed) in THF (10 ml), and the reaction mixture refluxed for about four hours. The mixture is poured into $H_2O$, extracted with diethyl ether, the etheral layer washed, dried and evaporated affording the desired product.

Treatment of the 3-oxo-compound of Step 3. above with $PCl_5/POCl_3$ followed by treatment with p-nitrophenol under conditions analogous to those described above affords the captioned precursor compound.

Treatment of the precursor compound with any one of the N-(bicyclic)alkylene primary amines described above affords compounds within the scope of Formula I.

EXAMPLE 15

The Preparation of N-Chlorosulfonyltrimethylsilylcarbamate 2-(Trimethylsilyl)ethanol (2.96 g) is added dropwise to a stirred solution of chlorosulfonylisocyanate (3.54 g) in carbon tetrachloride (8 ml) and cyclohexane (2 ml) under $N_2$ at RT. The reaction mixture is evaporated, yielding the sulfamoylation reagent which is used as is in the following examples.

EXAMPLE 16

The Preparation of 3-Amino-4-Isopropyl-5-(3-Methylphenoxy)-1,2,4,6-Thiatriazine-1,1-Dioxide Step 1. N,N-Dicyano-isopropylamine A solution of isopropylamine (39.9 g) in diethyl ether (110 ml) is added dropwise to a stirred solution of cyanogen bromide (100 g) in diethyl ether (150 ml) maintained at −5° C. The reaction mixture is stirred at RT overnight, filtered and the filtrate washed with diethyl ether. The washed filtrate and a solution of triethylamine (34.1 g) in diethyl ether (120 ml) are simultaneously added dropwise to a solution of cyanogen bromide (35.7 g) in diethyl ether (160 ml) maintained at −15° C., and the resulting mixture warmed to RT and stirred overnight. The mixture is filtered, washed, and evaporated affording a crude oil which is distilled, yielding the desired product as a clear oil, BP 52° C. (3.2 mm).

Step 2. N-cyano-N-[(3-methylphenoxy)imino]-isopropylamine

A solution of the isopropylamine from Step 1. above (21.5 g) in diethyl ether (75 ml) is added dropwise to a solution of m-cresol (21.0 g) in diethyl ether (50 ml) at RT. The reaction mixture is evaporated, distilled under high vacuum and the residue chromatographed (500 g silica; hexane; EtOAc), and the major fractions recrystallised from hexane, filtered and dried, yielding the desired product as a white crystalline solid, M.P.=56°-58° C.

Step 3. 3-Amino-4-isopropyl-5-(3-methylphenoxy)-1,2,4,6-thiatriazine-1,1-dioxide A solution of the sulfamoylation reagent from Example I above (13.4 g) in dichloromethane (150 ml) is added dropwise to a solution of the isopropylamine from Step 2. above (12.5 g) and triethylamine (5.9 g) in dichloromethane (150 ml) under $N_2$, and the reaction mixture stirred at RT overnight. Distilled water (100 ml) is added to the reaction mixture, resulting in formation of a precipitate, which is filtered, washed with methylene chloride and water and dried. The precipitate is recrystallized from MeOH and dried to yield the desired product as a white solid, M.P.>250° C. [NMR (DMSOd$_6$/TMS): 7.8(s, 2H), 7.5–6.9(m, 4H), 4.5(septet, J=6 Hz, 1H), 2.4(s, 3H), 1.5(d, J=6 Hz, 6H)].

EXAMPLE 17

The Preparation of 3-Amino-4-N-Butyl-5-(3-Methylphenoxy)-1,2,4,6-Thiatriazine-1,1-Dioxide Step 1. N,N-Dicyano-n-butylamine A solution of n-butylamine (49.3 g) in diethyl ether (100 ml) is added dropwise to a solution of cyanogen bromide (100 g) in diethyl ether (150 ml) at −10° C. over a period of 20 minutes. The reaction mixture is stirred at RT overnight and cooled, forming a precipitate which is filtered and washed. The filtrate and a solution of triethylamine (34.1 g) in diethyl ether (100 ml) are simultaneously added dropwise to a stirred solution of cyanogen bromide (35.7 g) in diethyl ether (200 ml) at −10° C. to −15° C. The reaction mixture is warmed to RT, filtered and washed, and the filtrate is evaporated and distilled affording the desired product, which is used without further purification in the next step.

Step 2. N-Cyano-N-[(3-methylphenoxy)imino]-n-butylamine

A solution of m-cresol (19.5 g) in diethyl ether (50 ml) is added dropwise at RT to a stirred solution of the butylamine from Step 1. above (22.2 g) in diethyl ether (75 ml) and the reaction mixture is stirred for about 60 hrs. The reaction mixture is evaporated and distilled under high vacuum. The residue is chromatographed (600 g silica gel; hex: EtOAc) and the major fractions combined and evaporated, yielding the desired product, which is used without further purification in the next step.

Step 3. 3-Amino-4-n-butyl-5-(3-methylphenoxy)-1,2,4,6-thiatriazine-1,1-dioxide

A solution of the sulfamoylation reagent from Example I above (5.8 g) in dichloromethane (30 ml) is added to a stirred solution of the n-butylamine from Step 2. above (5.8 g) and triethylamine (2.5 g) in dichloromethane (50 ml) under $N_2$. The reaction mixture is stirred at RT overnight. Distilled water (25 ml) is added to the reaction mixture, stirred for one hour, and then separated, filtered, washed with water and dried to yield the final product as a white solid, M.P.=208°-213° C., [NMR(DMSOd$_6$/TMS): 7.8(s, 2H), 7.5–7.0 (m, 4H), 4.1–3.9(t, J=8 Hz, 2H), 2.3(s, 3H), 1.9–1.2(m, 4H), 1.0–0.8(t, J=8 Hz, 3H)].

EXAMPLE 18

The Preparation of 5-Amino-2-Cyclohexyl-3-[3-[4-[1-(1-Piperidinyl)Indanyloxy]]Propylamino]]-2H-1,2,4,6-Thiatriazine-1,1-Dioxide Step 1. N-Carbomethoxy-N-cyclohexylsulfamoyl-O-methylisourea Triethylamine (112 g) is added to a stirred solution of N-carbomethoxy-O-methylisourea (132.1 g) in anhydrous THF (900 ml). The solution is cooled to −70° C. under an $N_2$ atmosphere and solution of cyclohexylsulfamoyl chloride (198 g) in anhydrous THF (400 ml) is added dropwise to the reaction mixture. The reaction mixture is warmed to RT filtered through Celite®, washed with anhydrous THF and evaporated to yield an oil which is taken up in methylene chloride, washed with 0.5N HCl and allowed to stand overnight. The organic layer is washed with 0.5N HCl, dried, filtered, washed with methylene chloride, evaporated and dried under high vacuum affording the desired product as an oil which is used in the next step without further purification.

Step 2. 2-Cyclohexyl-5-methoxy-2H-1,2,4,6-thiatriazin-3-one-1,1-dioxide

A solution of the isourea from Step 1. above (208.9 g) in anhydrous THF (500 ml) is added dropwise to a stirred suspension of 60% sodium hydride dispersion (57.0 g) in anhydrous THF (750 ml) and the reaction mixture is refluxed for 2 hours. Distilled water (450 ml) is added dropwise to the stirred mixture which is washed with diethyl ether. 20% sulfuric acid (400 ml) is added slowly to the stirred reaction mixture, which is extracted with methylene chloride, dried, filtered, and the filtrate evaporated and dried under high vacuum yielding the desired product as a crude solid which is used in the next step without further purification.

Step 3. 3-Chloro-2-cyclohexyl-5-methoxy-2H-1,2,4,6-thiatriazine-1,1-dioxide

A mixture of the thiatriazinone from Step 2. above (77.3 g) and phosphorus pentachloride (92.4 g) in phosphorus oxychloride (230 ml) is refluxed overnight. The reaction mixture is evaporated at 50° C. yielding an oil (92.3 g) which is used without further purification in the next step.

Step 4. 2-Cyclohexyl-5-methoxy-3-para-nitrophenoxy-2H-1,2,4,6-thiathiazine-1,1-dioxide A solution of the chlorothiatriazine obtained in Step 3. above (92.3 g) in methylene chloride (250 ml) is added dropwise to a stirred solution of para-nitrophenol (49.4 g) and pyridine (70.2 g) in methylene chloride (500 ml) and refluxed for 3 hours. The reaction mixture is washed with 3N HCl and sodium bicarbonate solution. The methylene chloride layer is dried, filtered, washed and evaporated yielding a solid which is dissolved in hot THF with charcoal, filtered and evaporated. The resulting solid is washed with diethyl ether, dissolved in methylene chloride, filtered through silica gel, washed with methylene chloride, filtered through Celite®, evaporated and triturated with diethyl ether affording a yellow solid. The solid is recrystallized from hot THF, yielding the desired product as a solid used in the next step without further purification.

Step 5. 2-Cyclohexyl-5-methoxy-3-[3-[4-[1-(1-piperidinyl)indanyloxy]]propylamino]-2H-1,2,4,6-thiatriazine-1,1-dioxide A solution of the para-nitrophenoxythiatriazine from Step 4. above (9.1 g) in methylene chloride (50 ml) is added dropwise to a mixture of 3-[4-[1-(piperidinyl)indanyloxy]]propylamine (5.5 g) and triethylamine (2.6 g) in methylene chloride (65 ml). The reaction mixture is washed with 0.5N HCl, H$_2$O, and sat'd NaHCO$_3$, and the organic layer dried, filtered, washed, and evaporated yielding a crude oil. The oil is chromatographed (silica gel: MeOH) and the fractions are combined, evaporated, dissolved in methylene chloride, and washed with sodium bicarbonate solution. The methylene chloride solution is dried, filtered, washed and evaporated yielding an oil which is used without further purification in the next step.

Step 6. 5-Amino-2-cyclohexyl-3-[3-[4-[1-(1-piperidinyl)indanyloxy]]propylamino]-2H-1,2,4,6,-thiatriazine-1,1-dioxide Condensed ammonia (15 ml) is poured into a bomb containing a cooled solution of the indanyloxythiatriazine from Step 5. above in methanol (50 ml). The bomb is sealed, heated overnight, cooled to RT and the reaction mixture evaporated. The residual oil is dissolved in ethyl acetate and chromatographed (silica gel/EtOAc). The major fractions are combined, evaporated, and treated with methylene chloride yielding a solid which is dissolved in diethyl ether, filtered, washed and dried affording the free base.

Step 7. 5-Amino-2-cyclohexyl-3-[3-[4-[1-(1-piperidinyl)indanyloxy]]propylamino]-2H-1,2,4,6-thiatriazine-1,1-dioxide tartrate A solution of tartaric acid (0.70 g) in isopropanol (50 ml) is added to a stirred solution of the free base from Step 6. above (2.6 g) in isopropanol (100 ml). The tartrate salt is filtered under N$_2$, washed and dried affording the salt as a white solid, MP=122°-132° C.

EXAMPLE 19

The Preparation of
5-Amino-4-Isopropyl-3-Para-Nitrophenoxy-2H-1,2,4,6-Thiatriazine-1,1-Dioxide Step 1. N,N-Dicyano-isopropylamine A solution of isopropylamine (79.7 g) in diethyl ether (200 ml) is added dropwise to a stirred solution of cyanogen bromide (200 g) in diethyl ether (500 ml) maintained at −10° C. The reaction suspension is warmed to room temperature overnight, filtered, washed with diethyl ether, and concentrated. The concentrated filtrate and a solution of triethylamine (68.2 g) in diethyl ether (94 ml) are simultaneously added dropwise to a solution of cyanogen bromide (71.7 g) in diethyl ether (300 ml) maintained at −15° C. The reaction mixture is warmed to room temperature overnight with stirring, filtered, washed with diethyl ether, evaporated and distilled under high vacuum affording the desired product as a clear liquid, B.P. 42° C. (0.5 mm).

Step 2. N-Cyano-N-[(para-nitrophenoxy)imino]isopropylamine

A solution of para-nitrophenol (11.5 g) in diethyl ether (30 ml) is added to a solution of the isopropylamine from Step 1. above (9.0 g) in diethyl ether (25 ml) at RT and stirred overnight. The reaction mixture is filtered, washed with diethyl ether and the filtered solid is dried yielding the desired product as a white solid, MP=132°-136° C.

Step 3. N-chlorosulfonyl-trimethylsilylcarbamate 2-(Trimethylsilyl)ethanol (1.2 g) is added dropwise to a stirred solution of chlorosulfonyl isocyanate (1.4 g) in carbon tetrachloride (8 ml) and methylene chloride (2 ml) under N$_2$ at RT. The reaction mixture is evaporated yielding the desired sulfamoylation reagent as a white solid used as is in the next step.

Step 4. 5-Amino-4-isopropyl-3-para-nitrophenoxy-2H-1,2,4,6-thiatriazine-1,1-dioxide A solution of the sulfamoylation reagent from Step 3. above (2.3 g) in methylene chloride (10 ml) is added dropwise to a stirred solution of the isopropylamine from Step 2. above (5.0 g) in methylene chloride (100 ml) under N$_2$ at RT. After 2 hours distilled water (25 ml) is added dropwise to the reaction mixture and the solution is stirred at RT overnight. The reaction mixture is extracted and the organic layer dried, filtered, and the filtrate evaporated. The residue is dissolved in methylene chloride and chromatographed (silica gel; CH$_2$Cl$_2$). The major fractions are combined and recrystallized from hot methanol affording the desired product as a white solid, MP >250° C.

EXAMPLE 20

The Preparation of
5-Amino-4-N-Butyl-3-(3-Methylphenoxy)-2H-1,2,4,6-Thiatriazine-1,1-Dioxide Step 1. N,N-Dicyano-butylamine A solution of butylamine (49.3 g) in diethyl ether (100 ml) is added dropwise to a stirred solution of cyanogen bromide (100 g) in diethyl ether (150 ml) maintained at −10° C. The reaction mixture is stirred at RT overnight, cooled, filtered, and the filtrate concentrated. The concentrate and a solution of triethylamine (34.1 g) in diethyl ether (100 ml) are simultaneously added dropwise to a stirred solution of cyanogen bromide (35.7 g) in diethyl ether (200 ml) maintained at −10° C. to −15° C. and the resulting mixture warmed to RT and stirred overnight. The mixture is filtered, washed, the filtrate evaporated and the residue distilled affording the desired product as a yellow liquid used in the next step without further purification.

Step 2. N-Cyano-N-[(3-methylphenoxy)imino]-n-butylamine

A solution of m-cresol (19.5 g) in diethyl ether (50 ml) is added dropwise at RT to a stirred solution of the n-butylamine obtained in Step 1. above (22.2 g) in diethyl ether (75 ml). The reaction mixture is evaporated, distilled, and the residue is chromatographed (silica gel:hexane/EtOAc) and the major fractions combined and evaporated affording the desired product as an oil which is used in the next step.

Step 3. N-Chlorosulfonyl-trimethylsilyl-carbamate 2-(Trimethylsilyl)ethanol (2.96 g) is added dropwise to a stirred solution of chlorosulfonyl isocyanate (3.54 g) in carbon tetrachloride (8 ml) and methylene chloride (2 ml) under N₂ at RT. The reaction mixture is evaporated yielding the sulfomoylation reagent as an oil which is used as is in the next step.

Step 4. 5-Amino-4-n-butyl-3-(3-methylphenoxy)-2H-1,2-4,6-thiatriazine-1,1-dioxide A solution of the sulfamoylation reagent obtained in Step 3. above (5.8 g) in methylene chloride (30 ml) is added dropwise to a stirred solution of the n-butylamine obtained in Step 2. above (5.8 g) and triethylamine (2.5 g) in methylene chloride (50 ml) under N₂ at RT. The reaction mixture is stirred overnight at RT, and distilled water (25 ml) added. The reaction mixture is stirred for one hour, separated, the organic layer washed with water, filtered and dried affording a solid which is recrystallized in hot methanol yielding the desired product as a solid, MP=217°-219° C.

EXAMPLE 21

The Preparation of 5-Amino-4-N-Butyl-3-[3-[5-[1-(1-Piperidinyl)-1,2,3,4-Tetrahydronaphthyloxy]Propylamino]]-2H-1,2,4,6-Thiatriazine-1,1-Dioxide.Tartrate A stirred solution of 3-[5-[1-(1-piperidinyl)-1,2,3,4-tetrahydronaphthyloxy]]propylamine (1 g) and 5-amino-4-n-butyl-3-(3-methylphenoxy)-2H-1,2,4,6-thiatriazine-1,1-dioxide (1 g) in pyridine (50 ml) is refluxed for about 60 hours. The reaction mixture is evaporated, chromatographed (silica gel; MeOH) and the slower-moving fractions combined, evaporated, the residual oil triturated with ether, and the solid filtered and dried, affording the desired products as the free base.

A solution of tartaric acid (2.5 g) in isopropanol (5 ml) is added to a stirred solution of the free base in isopropanol (20 ml) at RT. The precipitate is filtered, washed and recrystallized from isopropanol affording the desired product as a pink solid, M.P.=130° C. (dec).

Further examples of compounds within the scope of this invention include the following:

5-Amino-4-n-butyl-3-[3-[4-[1-(1-piperidinyl)indanyloxy]]propylamino]-2H-1,2,4,6-thiatriazine-1,1-dioxide tartrate isopranolate, M.P.=125° C. (dec); and 5-Amino-4-isopropyl-3-[3-[4-[1-(1-piperidinyl)indanyloxy]]propylamino]-2H-1,2,4,6-thiatriazine-1,1-dioxide tartrate isopropanolate, M.P.=69° C. (dec).

Additional representative examples of compounds within the scope of Formula I which may be prepared according to the reaction sequences described above are disclosed in Tables I, and II, below.

TABLE I

[Structure: tetrahydronaphthalene with (CH₂)ₐ-NR₈R₉ substituent, connected via O—(CH₂)ₙ—NH— to thiatriazine ring bearing R₁ and NH₂]

| a | n | NR₈R₉ | R₁ |
|---|---|---|---|
| 0 | 3 | NH₂ | 2-CH₃ |
| 0 | 3 | NHCH₃ | 4-CH₃ |
| 0 | 3 | N(CH₃)₂ | 2-C₂H₅ |
| 0 | 3 | piperidinyl | 4-C₂H₅ |
| 0 | 3 | morpholinyl | 2-n-propyl |
| 0 | 4 | piperidinyl | 4-n-propyl |
| 0 | 4 | morpholinyl | 2-CH₃ |
| 0 | 4 | pyrrolidinyl | 4-CH₃ |
| 0 | 4 | pyrrolidinyl | 2-C₂H₅ |
| 0 | 4 | NH₂ | 4-C₂H₅ |
| 0 | 3 | pyrrolidinyl | 2-n-propyl |
| 1 | 3 | NH₂ | 4-n-propyl |
| 1 | 3 | NHCH₃ | 2-CH₃ |
| 1 | 3 | N(CH₃)₂ | 4-CH₃ |
| 1 | 3 | piperidinyl | 2-C₂H₅ |
| 1 | 3 | morpholinyl | 4-C₂H₅ |
| 1 | 4 | piperidinyl | 2-n-propyl |
| 1 | 4 | morpholinyl | 4-n-propyl |

TABLE I-continued

Structure: tetrahydronaphthalene with (CH2)a-NR8R9 substituent, O-(CH2)n-NH-C(=N-S(O2)-N=)-C(R1)-NH2 thiadiazine group

| a | n | NR8R9 | R1 |
|---|---|---|---|
| 1 | 4 | pyrrolidinyl | 2-CH3 |
| 1 | 4 | pyrrolidinyl | 4-CH3 |
| 1 | 4 | NH2 | 2-C2H5 |
| 1 | 4 | NHCH3 | 4-C2H5 |
| 0 | 4 | NH2 | 6-CH3 |
| 0 | 4 | NH2 | 6-C2H5 |
| 0 | 4 | NH2 | 6-n-propyl |
| 0 | 4 | NH2 | 6-i-propyl |
| 0 | 4 | NH2 | 6-n-butyl |
| 0 | 4 | NH2 | 6-benzyl |
| 0 | 4 | NH2 | 6-cyclohexyl |
| 0 | 3 | pyrrolidinyl | 6-CH3 |
| 0 | 3 | pyrrolidinyl | 6-C2H5 |
| 0 | 3 | pyrrolidinyl | 6-n-propyl |
| 0 | 3 | pyrrolidinyl | 6-i-propyl |
| 0 | 3 | pyrrolidinyl | 6-n-butyl |
| 0 | 3 | pyrrolidinyl | 6-benzyl |
| 0 | 3 | pyrrolidinyl | 6-cyclohexyl |
| 1 | 3 | NH2 | 6-CH3 |
| 1 | 3 | pyrrolidinyl | 6-C2H5 |
| 1 | 3 | NH2 | 6-n-propyl |
| 1 | 3 | NHCH3 | 6-i-propyl |
| 1 | 3 | N(CH3)2 | 6-n-butyl |
| 1 | 3 | piperidinyl | 6-benzyl |
| 1 | 3 | morpholinyl | 6-cyclohexyl |
| 1 | 3 | piperidinyl | 6-CH3 |
| 1 | 3 | morpholinyl | 6-C2H5 |
| 1 | 3 | pyrrolidinyl | 6-n-propyl |
| 1 | 3 | pyrrolidinyl | 6-i-propyl |
| 1 | 3 | NH2 | 6-n-butyl |
| 1 | 3 | NHCH3 | 6-benzyl |
| 1 | 4 | NH2 | 6-cyclohexyl |
| 1 | 4 | pyrrolidinyl | 6-CH3 |
| 1 | 4 | NH2 | 6-C2H5 |
| 1 | 4 | NHCH3 | 6-n-propyl |
| 1 | 4 | N(CH3)2 | 6-i-propyl |
| 1 | 4 | piperidinyl | 6-n-butyl |
| 1 | 4 | morpholinyl | 6-benzyl |

TABLE I-continued

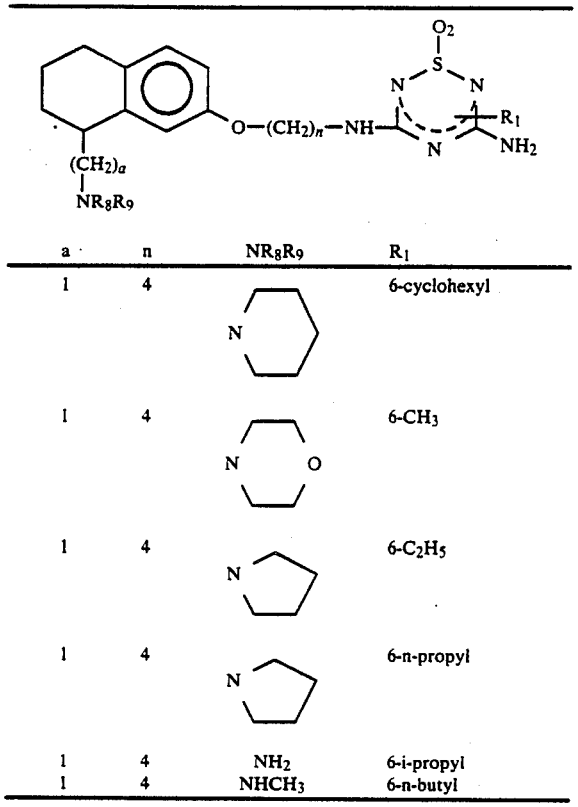

| a | n | NR₈R₉ | R₁ |
|---|---|---|---|
| 1 | 4 | piperidinyl | 6-cyclohexyl |
| 1 | 4 | morpholinyl | 6-CH₃ |
| 1 | 4 | pyrrolidinyl | 6-C₂H₅ |
| 1 | 4 | pyrrolidinyl | 6-n-propyl |
| 1 | 4 | NH₂ | 6-i-propyl |
| 1 | 4 | NHCH₃ | 6-n-butyl |

TABLE II

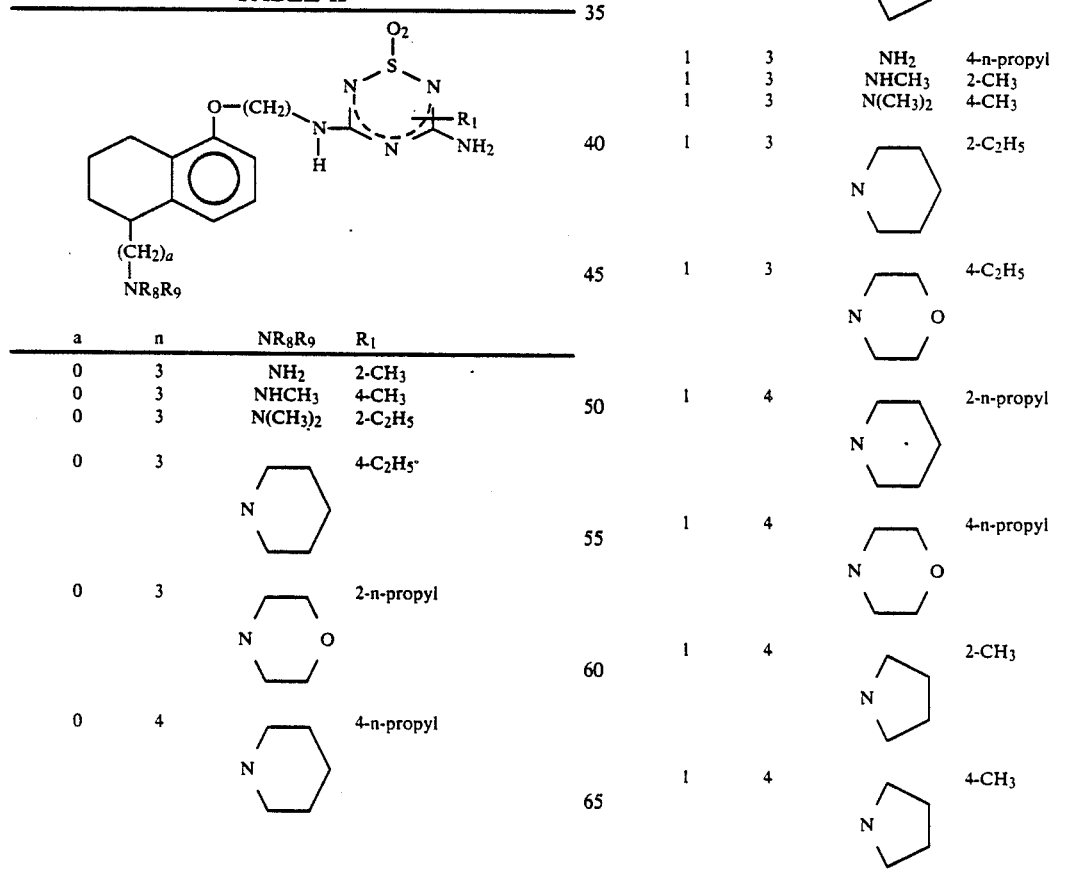

| a | n | NR₈R₉ | R₁ |
|---|---|---|---|
| 0 | 3 | NH₂ | 2-CH₃ |
| 0 | 3 | NHCH₃ | 4-CH₃ |
| 0 | 3 | N(CH₃)₂ | 2-C₂H₅ |
| 0 | 3 | piperidinyl | 4-C₂H₅ |
| 0 | 3 | morpholinyl | 2-n-propyl |
| 0 | 4 | piperidinyl | 4-n-propyl |

TABLE II-continued

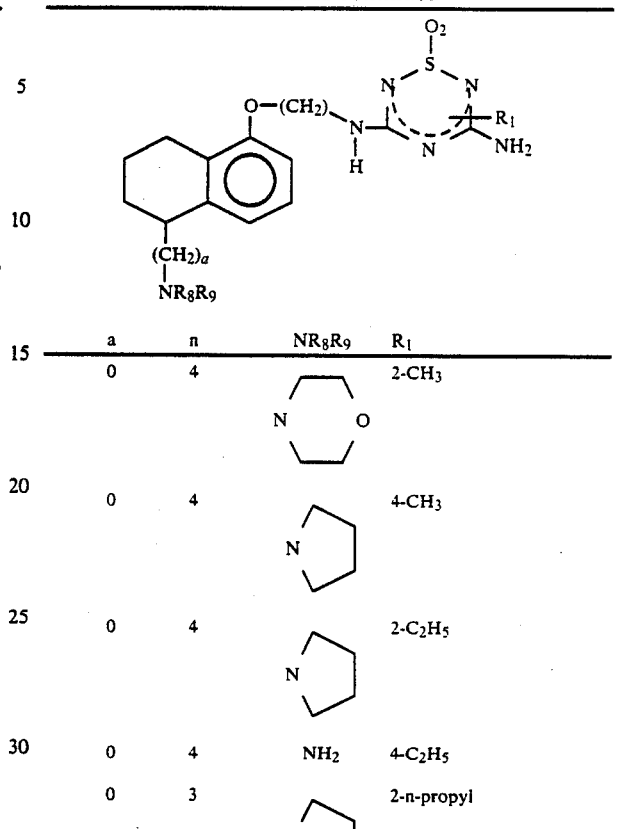

| a | n | NR₈R₉ | R₁ |
|---|---|---|---|
| 0 | 4 | morpholinyl | 2-CH₃ |
| 0 | 4 | pyrrolidinyl | 4-CH₃ |
| 0 | 4 | pyrrolidinyl | 2-C₂H₅ |
| 0 | 4 | NH₂ | 4-C₂H₅ |
| 0 | 3 | pyrrolidinyl | 2-n-propyl |
| 1 | 3 | NH₂ | 4-n-propyl |
| 1 | 3 | NHCH₃ | 2-CH₃ |
| 1 | 3 | N(CH₃)₂ | 4-CH₃ |
| 1 | 3 | piperidinyl | 2-C₂H₅ |
| 1 | 3 | morpholinyl | 4-C₂H₅ |
| 1 | 4 | piperidinyl | 2-n-propyl |
| 1 | 4 | morpholinyl | 4-n-propyl |
| 1 | 4 | pyrrolidinyl | 2-CH₃ |
| 1 | 4 | pyrrolidinyl | 4-CH₃ |

TABLE II-continued

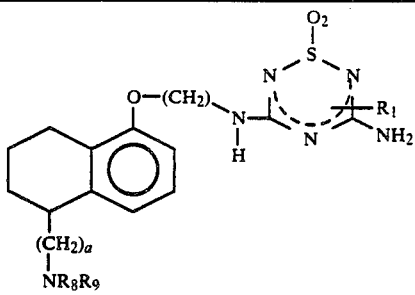

| a | n | NR8R9 | R1 |
|---|---|---|---|
| 1 | 4 | NH2 | 2-C2H5 |
| 1 | 4 | NHCH3 | 4-C2H5 |
| 0 | 3 | pyrrolidinyl | 6-CH3 |
| 0 | 3 | pyrrolidinyl | 6-C2H5 |
| 0 | 3 | pyrrolidinyl | 6-n-propyl |
| 0 | 3 | pyrrolidinyl | 6-i-propyl |
| 0 | 3 | pyrrolidinyl | 6-n-butyl |
| 0 | 3 | pyrrolidinyl | 6-benzyl |
| 0 | 3 | pyrrolidinyl | 6-cyclohexyl |
| 1 | 3 | morpholinyl | 6-CH3 |
| 1 | 3 | pyrrolidinyl | 6-C2H5 |
| 1 | 3 | pyrrolidinyl | 6-n-propyl |
| 1 | 3 | NH2 | 6-i-propyl |
| 1 | 3 | NHCH3 | 6-n-butyl |
| 1 | 3 | N(CH3)2 | 6-benzyl |
| 1 | 3 | piperidinyl | 6-cyclohexyl |
| 1 | 3 | NH2 | 6-CH3 |
| 1 | 3 | NHCH3 | 6-C2H5 |

TABLE II-continued

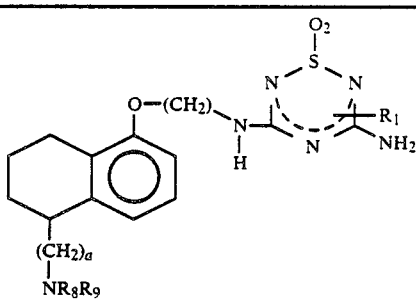

| a | n | NR8R9 | R1 |
|---|---|---|---|
| 1 | 3 | N(CH3)2 | 6-n-propyl |
| 1 | 3 | piperidinyl | 6-i-propyl |
| 1 | 3 | morpholinyl | 6-n-butyl |
| 1 | 3 | piperidinyl | 6-benzyl |
| 1 | 3 | morpholinyl | 6-cyclohexyl |
| 1 | 3 | pyrrolidinyl | 6-CH3 |
| 1 | 4 | pyrrolidinyl | 6-C2H5 |
| 1 | 4 | NH2 | 6-n-propyl |
| 1 | 4 | NHCH3 | 6-i-propyl |
| 1 | 4 | pyrrolidinyl | 6-n-butyl |
| 1 | 4 | NH2 | 6-benzyl |
| 1 | 4 | NHCH3 | 6-cyclohexyl |
| 1 | 4 | N(CH3)2 | 6-CH3 |
| 1 | 4 | piperidinyl | 6-C2H5 |
| 1 | 4 | morpholinyl | 6-n-propyl |
| 1 | 4 | pyrrolidinyl | 6-i-propyl |

TABLE II-continued

[Structure: tetrahydronaphthalene with O—(CH$_2$)$_n$—NH—C(=N)—NH— linked to a 1,2,4-thiadiazine ring bearing SO$_2$, R$_1$, and NH$_2$ substituents; with (CH$_2$)$_a$—NR$_8$R$_9$ substituent]

| a | n | NR$_8$R$_9$ | R$_1$ |
|---|---|---|---|
| 1 | 4 | morpholino (N–O ring) | 6-n-butyl |
| 1 | 4 | pyrrolidino | 6-benzyl |
| 1 | 4 | pyrrolidino | 6-cyclohexyl |
| 1 | 4 | NH$_2$ | 6-CH$_3$ |
| 1 | 4 | NHCH$_3$ | 6-C$_2$H$_5$ |

Various tests in animals have been carried out to show the ability of the compounds of this invention to exhibit pharmacological responses that can be correlated with activity in humans. These tests involve such factors as the effect of the compounds of Formula I on gastric secretion and their H$_2$ antagonist, anti-ulcer and cytoprotective activity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine H$_2$-receptor antagonists by the results obtained in the following H$_2$-antagonist tests.

A. Isolated Guinea Pig Atria

The H$_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound*. Vol. 1, Academic Press (1964).

1. Tissue Bath

A fifty ml jacketed tissue bath is maintained at 30° C. The bath consists of a Krebs-Henseleit buffer aerated with 95% O$_2$-5% CO$_2$, (pH 7.4). The buffer is prepared by mixing: 4 ml of an aqueous (distilled deionized) solution of CaCl$_2$.2H$_2$O (0.37 g/ml); 4 ml of an aqueous (distilled deionized) solution of MgSO$_4$.7H$_2$O (0.29 g/ml); 7.2 g of glucose; and, 2 liters of aqueous (distilled deionized) solution containing NaCl (28 g), NaHCO$_2$ (8.4 g), KCl (1.4 g) and KH$_2$PO$_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taper-point needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0M histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100M then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages (±SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10× magnifying glass; the following scale is employed:

| Grade | Description |
|---|---|
| 0 | No lesions |
| 1 | 5 lesions, all < 2 mm |
| 2 | 5 lesions, at least 1 > 2 mm |
| 3 | 5–10 lesions, all < 2 mm |
| 4 | 5–10 lesions, at least 1 > 2 mm |
| 5 | 10 lesions, all < 2 mm |
| 6 | 10 lesions, at least 1 > 2 mm |
| 7 | Perforation |

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150–200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2×–10× magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The results of the anti-secretory, anti-ulcer and cytoprotective assays, detailed above, establish the utility of the compounds of the present invention in the treatment of peptic ulcers in mammals, including humans. These compounds both aid in the healing of such ulcers and also prevent their formation.

The most preferred cytoprotective compounds are the 5-amino-3-[3-[5-[1-(1-piperidinyl)-1,2,3,4-tetrahydronaphthyloxy]]propylamino]-2H-1,2,4,6-thiatriazine-1,1-dioxide compounds wherein the 2-position is substituted by methyl, n-butyl and benzyl.

Compounds of the present invention which exhibit a preferred combination of cytoprotective and H₂-antagonistic properties comprise compounds within the scope of Formulae I to V wherein the thiatriazine moiety is substituted in the 6-position with an alkyl radical, preferably lower alkyl and most preferably n-butyl.

In particular, the compounds according to Formulae I and II are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, H₁-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which ensures maximum thereapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula

wherein:
X is halo; and
R is lower alkyl or haloloweralkyl.

* * * * *